United States Patent [19]

Hasegawa et al.

[11] 4,321,256

[45] Mar. 23, 1982

[54] SHAMPOO CONTAINING A POLYGLYCOL-POLYAMINE CONDENSATION RESIN AND A PHOSPHATE ESTER

[75] Inventors: Tatsuru Hasegawa, Machida; Yasuo Ohmi; Guy A. G. Ricketts, both of Tokyo, all of Japan; Stuart J. Sime, Little Sutton, England

[73] Assignee: Lever Brothers Company, New York, N.Y.

[21] Appl. No.: 167,977

[22] Filed: Jul. 14, 1980

[30] Foreign Application Priority Data

Jul. 19, 1979 [GB] United Kingdom .............. 25175/79

[51] Int. Cl.³ .................. A61K 7/08; C11D 1/29; C11D 1/78; C11D 3/37
[52] U.S. Cl. ........................................ 424/70; 252/90; 252/174.16; 252/174.23; 252/544; 252/548; 252/DIG. 13
[58] Field of Search .................. 252/544, 548, 174.16, 252/DIG. 13, 90, 551; 424/70

[56] References Cited

U.S. PATENT DOCUMENTS

| | | | |
|---|---|---|---|
| 3,987,162 | 10/1976 | Scheuermann | 252/DIG. 13 X |
| 3,987,162 | 10/1976 | Scheuermann | 252/114 X |
| 4,132,679 | 1/1979 | Tsutsumi et al. | 252/DIG. 13 X |
| 4,139,485 | 2/1979 | Imokawa et al. | 252/DIG. 13 X |

FOREIGN PATENT DOCUMENTS

| | | |
|---|---|---|
| 2255050 | 7/1975 | France . |
| 2370090 | 6/1978 | France . |
| 54-134712 | 10/1979 | Japan . |
| 1538174 | 1/1979 | United Kingdom . |

OTHER PUBLICATIONS

Household and Personal Products Industry, vol. 16, No. 6, Jun. 1979, p. 22.

*Primary Examiner*—Dennis L. Albrecht
*Attorney, Agent, or Firm*—Irving N. Feit; James J. Farrell; Melvin H. Kurtz

[57] ABSTRACT

An aqueous shampoo containing a hair conditioning agent comprises an alkyl sulfate or alkyl ether sulfate detergent, a polyglycol-polyamine condensation resin and a phosphate mono- or di-ester. The deposition onto hair of the polyglycol-polyamine condensation resin from the shampoo is enhanced by the presence of the phosphate esters.

5 Claims, No Drawings

SHAMPOO CONTAINING A POLYGLYCOL-POLYAMINE CONDENSATION RESIN AND A PHOSPHATE ESTER

The invention relates to shampoos, particularly to shampoos which contain a polymer as a hair conditioning agent.

Certain polymers can be incorporated into aqueous liquid shampoos for deposition onto the hair during the shampooing process. These polymers can thereby impart useful conditioning benefits to the hair, such as improved ease of combing while the hair is still wet. Generally, any benefit obtained is dependent upon the amount of the polymer left on the hair after the shampooing and rinsing procedures. The magnitude of the benefit obtained is therefore usually dependent on the amount of the polymer present in the shampoo.

It has been proposed, for example in U.S. Patent Specification No. 3 987 162 (assigned to Henkel & Ci GmbH), to treat the hair with a shampoo containing readily soluble, hardenable polycondensation products which are the reaction products of water-soluble polyamines with polyoxyalkylene glycol derivatives reacted with a bifunctional compound containing more than one epoxide and/or α-halo-β-hydroxy alkyl groups in the molecule. Hair so treated is stated to have excellent, lasting combability with softness and body, but there is no evidence to attribute this to improved substantivity of the polycondensation product to the hair.

Shampoo formulators have been concerned with devising ways of modifying shampoo formulae so as to increase the degree by which polymers of this type can be deposited on the hair so as either to enhance the conditioning effect or to be able to produce the same effect through the use of less of the polymer.

Of the polymers which have more recently become of interest to shampoo formulators as potentially useful hair conditioning agents are polyglycol-polyamine condensation resins.

Of the detergents used in formulating shampoos the alkyl sulphate and alkyl ether sulphate anionic detergents are the most widely used. It is with the enhancement of the deposition of polyglycol-polyamine condensation resins from such anionic detergent-based shampoos that the present invention is concerned.

The invention is based on the discovery that deposition onto the hair of a polyglycol-polyamine condensation resin, as a conditioning agent from a shampoo based on an alkyl sulphate or alkyl ether sulphate detergent is enhanced by including in the shampoo certain anionic additives.

Accordingly, the invention provides an aqueous shampoo comprising:

(A) from 5% to 30% by weight of an alkyl sulphate or alkyl ether sulphate detergent;

(B) from 0.1% to 5% by weight of a polyglycol-polyamine condensation resin; and (C) from 0.1% to 3% by weight of a phosphate ester comprising a monoester of the formula

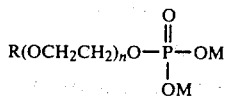

and/or a diester of the formula

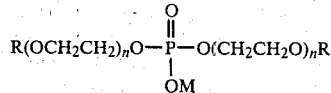

where

R is an hydrocarbon group having from 8 to 22 carbon atoms;

n is 0 or an integer of from 1 to 10; and

M is hydrogen or an alkali metal, ammonium or amine salt forming group.

The detergent employed in the shampoo of this invention is an alkyl sulphate or alkyl ether sulphate. Commonly used detergents of these kinds are the $C_{10}$–$C_{18}$ alkyl sulphates and $C_{10}$–$C_{18}$ alkyl ether sulphates containing 2 or 3 moles of ethylene oxide. These detergents are generally employed in the form of their sodium, potassium, ammonium or mono-, di- or tri-ethanolamine salts. Examples of these detergents are sodium lauryl sulphate, ammonium lauryl sulphate, mono-, di- and tri-ethanolammonium lauryl sulphates, sodium lauryl ether sulphate (2 $\overline{EO}$), sodium lauryl ether sulphate (3 $\overline{EO}$), potassium lauryl ether sulphate (2 $\overline{EO}$) and ammonium lauryl ether sulphate (3 $\overline{EO}$). The shampoo will generally contain from 5% to 30% by weight of anionic detergent.

Shampoos containing less than about 5% by weight of anionic detergent are likely in use to produce insufficient lather to clean the hair efficiently, while shampoos containing more than 30% by weight of anionic detergent may be too thick to apply conveniently to the hair and may also degrease the hair to an undesirably excessive degree.

The polymeric hair conditioning ingredient is a polyglycol-polyamine condensation resin which is a hardenable polycondensation product produced by reacting a polyamine compound having from 2 to 10 carbon atoms with an ether of polyoxyalkylene glycol having terminal halogens or hydroxyls and having from 2 to 4 carbon atoms in the alkylene units thereof, said polyamine reaction compounds having more than one hydrogen atom attached to a nitrogen atom and being further reacted with a bifunctional aliphatic compound having functional groups selected from the group consisting of epoxide and α-halo-β-hydroxy-alkyl.

Preferably, the polycondensation product is a reaction product selected from the group consisting of (i) the reaction product of dipropylenetriamine, bischlorohydrin ether of polyoxyethylene glycol having an average molecular weight of about 1,000 and epichlorohydrin, (ii) the reaction product of dipropylenetriamine, bischlorohydrin ether of polyoxyethylene glycol having an average molecular weight of about 1,000, and bischlorohydrin ether of polyoxyethylene glycol having an average molecular weight of about 600.

(iii) the reaction product of diethylenetriamine, ethoxylated ethylene chlorohydrin, and epichlorohydrin, (iv) the reaction product of dipropylenetriamine, ethoxylated glycerin chlorohydrin ether, and epichlorohydrin, (v) the reaction product of triethylenetetramine, bischlorohydrin ether of polyoxyethylene glycol having an average molecular weight of about 1,000, and bischlorohydrin ether of polyoxyethylene glycol having an average molecular weight of about 600, (vi) the reaction product of dipropylenetriamine and bis-chlorohydrin ether of polyoxyethylene glycol having an average molecular weight of about 600, and (vii) the reaction product of dipropylenetriamine and bis-chlorohydrin ether of polyoxyethylene glycol having an average molecular weight of about 200, wherein the ratio of chlorine atoms to amino hydrogen atoms in the reaction products is 4:5 to 7:5.

The identity of resins prepared in accordance with the above directions is further described in U.S. Pat. No. 3,987,162 assigned to Henkel & Cie GmbH, the disclosure of which is incorporated herein by reference.

The preferred polyglycol-polyamine condensation resin for use in shampoos according to the invention is that which is available commercially under the trade name POLYQUART H from Henkel & Cie GmbH, as a 50% aqueous solution. POLYQUART H is a trade mark.

The polyglycol-polyamine condensation resin is present in the shampoo of the invention in an amount of from 0.1% to 5% based on the weight of the shampoo. Preferred amounts are from 0.2% to 3% by weight.

Shampoos containing less than 0.1% by weight of the resins are likely in use to lead to little or no improvement in the ease of wet combing of shampooed hair compared to the use of a similar shampoo from which the resin has been omitted altogether, while shampoos containing more than 5% by weight of the resin are unlikely in use to further improve the ease of wet combing beyond that achieved when using a shampoo containing 5% by weight of the resin.

The phosphate ester of the shampoo according to the invention comprises a monoester of the formula

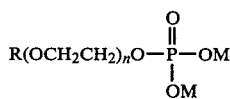

and/or a diester of the formula

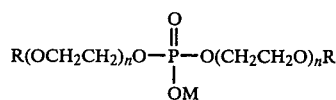

where

R is an hydrocarbon group having from 8 to 22 carbon atoms;

n is 0 or an integer of from 1 to 10; and

M is hydrogen or an alkali metal, ammonium or amine salt forming group.

The hydrocarbon group R is preferably one chosen from alkyl, alkenyl, cycloalkyl or cycloalkenyl groups.

When the group M is an alkali metal, it is preferably sodium or potassium, and when the group M is an amine salt forming group it can be a substituted ammonium group, particularly the lower alkyl and hydroxy lower alkyl groups, especially the mono-, di- and tri-ethyl, propyl, hydroxyethyl and hydroxypropyl-substituted ammonium groups.

The phosphate ester is usually produced commercially as a mixture of the mono- and di-esters defined above. They are available commercially under various trade names, for example, BEROL, BRIPHOS, CRODAFOS and HOSTAPHAT. BEROL 729 has alkyl chain lengths of 16–18 carbon atoms and contains series of 4 ethylene oxide units. In BRIPHOS L2D the alkyl chains are lauryl groups and it contains series of 2 ethylene oxide units. In BRIPHOS O3D and CRODAFOS N3N the alkyl groups are oleyl and the ethylene oxide groups comprise 3 units. In HOSTAPHAT KO 3OON, mon-, di- and tri-phosphoric esters of oleic acid are present. For mono- and di-ester mixtures, the weight ratio of mono-ester to di-ester may vary, typically from 1:10 to 10:1. Preferred phosphate esters are those in which n is 0 or an integer of from 1 to 6, in the structural formulae set out hereinbefore.

The phosphate ester is included in the shampoo in an amount of 0.1% to 3% by weight of the shampoo, preferably from 0.2% to 2.5% by weight.

Shampoos containing less than 0.1% by weight of the phosphate ester are unlikely in use to improve the deposition on the hair of the polymer beyond that which occurs when the phosphate ester is omitted altogether, while shampoos containing more than 3% by weight of the phosphate ester may lead to competitive deposition of both the polymer and the phosphate ester leading to poor conditioning results.

The shampoo of the invention may also include minor amounts of other ingredients which are commonly employed in shampoos, for example foam booster, thickener, opacifier, perfume, colouring agent, preservative, proteins, and an agent for adjusting pH, the latter usually being in the range 4 to 9 and is preferably from 5.5 to 7.5.

The shampoo can be formulated as a clear shampoo or as an opaque shampoo, depending upon consumer preference and available packaging.

The degree to which the polyglycol-polyamine condensation resin is deposited on the hair, and the influence of the phosphate ester on this, can be assessed by examining three properties which result from washing hair with the shampoo. Firstly, it has been shown that the time taken to comb out, that is to de-tangle, a switch of wet shampooed hair is less when both the resin and the ester are present in the shampoo, then when either is omitted. This is indicative of improved conditioning, recognised by the consumer as easier wet combing, when the shampoo of the invention is employed. Secondly, it has been shown that the foam volume of the shampoo on the hair is greater when both resin and ester are present in the shampoo, than when either is omitted. The ester in the absence of the resin may even depress the foam volume. Thirdly, the foam-stability, which can also be recognised as creaminess, is likewise improved when both resin and ester are present in the shampoo, than when either is omitted. The improvement of both foam volume and stability are also seen as desirable attributes which the consumer will readily recognise when using the shampoo of the invention.

Evidence to support the first of these benefits, that is the wet combing benefit attributable to the improved deposition of the polymer on the hair due to the presence of the ester, can be obtained from a comparative wet combing experiment, an example of which is described below.

Experiment 1

Ease of combing and detangling of wet hair

Materials and Method

Three test shampoos having the following formulations were prepared:

|  | % w/w | | |
| --- | --- | --- | --- |
|  | A | B | C |
| Sodium lauryl ether sulphate | | | |
| (2 OE), 100% active | 11.6 | 11.6 | 11.6 |
| POLYQUART H, 50% active | 2.0 | 1.0 | — |
| BRIPHOS 03D | — | 1.0 | 2.0 |
| Water | to 100 | 100 | 100 |

The pH of each of the test shampoos was adjusted to pH 6.5 with caustic soda.

A 16% by weight solution of the detergent, monoethanolamine lauryl sulphate, was prepared as a control 'shampoo'.

Standard switches of dark hair (10 g and approximately 25 cm long) were first washed with monoethanolamine lauryl sulphate solution as a standard detergent and then rinsed with water to provide clean switches. Each switch was then combed while still wet and the time taken to comb out each switch was recorded as control values for combability. The control values for each switch were different.

Each switch was then treated with Shampoos A, B or C, rinsed with water as before and then again wet combed to provide a new value for combability. The percentage reduction in wet combing time was then calculated in each case.

Results

The results were subjected to statistical analysis and were summarised in terms of the percentage reduction in combing time for each test treatment as compared with the control treatment. These results are summarised in the following Table.

|  | % reduction in combing time compared to control |
| --- | --- |
| Shampoo A | 27 |
| Shampoo B | 47 |
| Shampoo C | 40 |

These results demonstrate that the time taken to detangle a wet hair switch is less when both the polymer and phosphate ester is present in the shampoo (B), than when either is omitted (A and C).

Evidence to support the second and third of these benefits, that is the increase in both foam volume and foam stability (creaminess) attributable to the presence in the shampoo of both the polymer and the ester, can be obtained from a comparative experiment in which foam volume and creaminess are assessed subjectively by a panel of trained assessors. An example of such a comparative experiment is described below.

Experiment 2

Assessment of foam volume and stability

Materials and Method

Three test shampoos having the following formulations were prepared:

|  | % w/w | | |
| --- | --- | --- | --- |
|  | D | E | F |
| Sodium lauryl ether sulphate | | | |
| (2 EO), 100% active | 12.1 | 12.1 | 12.1 |
| POLYQUART H, 50% active | 1.5 | 2.5 | — |
| BRIPHOS 03D | 1.0 | — | 2.5 |
| Opacifier | 9.0 | 9.0 | 9.0 |
| Alkyl dimethyl betaine } foam boosters | 1.0 | 1.0 | 1.0 |
| Coconut alkanolamide | 1.5 | 1.5 | 1.5 |
| NaCl, 20% aqueous solution for viscosity control | 2.0 | 1.0 | — |
| Preservative | 0.25 | 0.25 | 0.25 |
| Water to | 100 | 100 | 100 |
| pH (adjusted with NaOH) | 5.8 | 5.5 | 5.4 |
| Viscosity at 25° C. (cps) | 1360 | 1460 | 1330 |

Strips of moistened plastic sponge and impregnated with a standard quantity of each shampoo were massaged between the fingers following a standard pattern for a standard time by a panel of trained assessors. The assessors first applied a little grease to their hands to simulate the presence of natural grease on the hair. They then employed a left and right hand pair of comparison test to determine which of either sample (chosen from shampoos D, E and F) generated the greater foam volume and the greater creaminess (as an index of foam stability). The test was set up and the result analysed statistically: none of the assessors knew the identity of the shampoos under test.

The test was carried out twice.

Results

The assessors' preference for foam volume (i.e. the higher the foam volume the greater the preference) are summarised in the following Table.

|  | Preference for foam volume | |
| --- | --- | --- |
| Comparison | Test 1 | Test 2 |
| Shampoo D vs Shampoo E | D | D |
| Shampoo D vs Shampoo F | D | D |

The assessors' preference for creaminess (i.e. the creamier the foam, the greater the preference) are summarised in the following Table.

|  | Preference for creaminess of foam | |
| --- | --- | --- |
| Comparison | Test 1 | Test 2 |
| Shampoo D vs Shampoo E | D | D |
| Shampoo D vs Shampoo F | D | D |

These results demonstrate that the shampoo containing both the polymer and phosphate ester (D) was capable of being lathered to a greater foam volume with a greater stability, as determined by its creamy feel, than shampoos from which either is omitted (E and F).

The invention also provides a process for preparing an aqueous shampoo which comprises mixing together from 5% to 30% by weight of an alkyl sulphate or an alkyl ether sulphate detergent; from 0.1% to 5% by weight of a polyglycol-polyamine condensation resin; and from 0.1% to 3% by weight of a phosphate ester, each ingredient as herein defined.

The invention further provides a method of treating hair which comprises applying to hair an effective amount of an aqueous shampoo as herein defined.

The invention furthermore provides a a closed container or dispenser containing an aqueous shampoo as herein defined.

The invention is illustrated by the following Examples of aqueous shampoo formulations, in which Examples 1 to 4 are clear shampoos and Example 5 is an opaque shampoo.

EXAMPLE 1

| | % w/w |
|---|---|
| Sodium lauryl ether sulphate (2 EO): 21% AD | 41.1 |
| Lauryl dimethylamino acetic acid betaine: 30% AD | 4 |
| Coconut fatty acid diethanolamide | 1.5 |
| Oleyl triethoxy phosphate (BRIPHOS 03D) | 1 |
| Polyglycol-polyamine condensation resin (POLYQUART H): 50% active | 1.5 |
| Preservative, colouring matter, salt | 0.58 |
| Water | to 100 |

The shampoo had a pH of 6 a viscosity of 1500 cp at 25° C.

EXAMPLE 2

| | % w/w |
|---|---|
| Sodium lauryl ether sulphate (2 EO): 100% AD | 12.0 |
| POLYQUART H: 50% active | 2.5 |
| BRIPHOS 03D | 2.5 |
| Water | to 100 |
| pH adjusted to 6.5 | |

EXAMPLE 3

| | % w/w |
|---|---|
| Monoethanolamine lauryl sulphate: 100% AD | 20.0 |
| POLYQUART H: 50% active | 3.0 |
| BRIPHOS 03D | 1.7 |
| Coconut diethanolamide | 5.0 |
| Water | to 100 |
| pH adjusted to 6.5 | |

EXAMPLE 4

| | % w/w |
|---|---|
| Sodium lauryl ether sulphate (3 EO): 100% AD | 12.0 |
| POLYQUART H: 50% active | 0.3 |
| BRIPHOS 03D | 1.0 |
| Water | to 100 |
| pH adjusted to 6.5 | |

EXAMPLE 5

| | % w/w |
|---|---|
| Sodium lauryl ether sulphate (2 EO): 100% AD | 12.0 |
| POLYQUART H: 50% active | 3.0 |
| BRIPHOS 03D | 1.0 |
| Opacifier | 9.0 |
| Water | to 100 |
| pH adjusted to 6.5. | |

We claim:
1. An aqueous shampoo comprising:
(a) from 5% to 30% by weight of an alkyl sulphate or alkyl ether sulphate detergent;
(b) from 0.1% to 5% by weight of a polyglycol condensation resin which is a hardenable polycondensation product produced by reacting a polyamine compound having from 2 to 10 carbon atoms with an ether of polyoxyalkylene glycol having terminal halogens or hydroxyls and having from 2 to 4 carbon atoms in alkylene units thereof, said polyamine reaction compounds having more than one hydrogen atoms attached to a nitrogen atom and being further reacted with a bifunctional aliphatic compound having functional groups selected from the group consisting of epoxide and α-halo-β-hydroxy-alkyl; and
(c) from 0.1% to 3% by weight of a phosphate ester comprising a monoester of the formula

$$R(OCH_2CH_2)_nO-\underset{\underset{OM}{|}}{\overset{\overset{O}{\|}}{P}}-OM$$

and or a diester of the formula $$R(OCH_2CH_2)_nO-\underset{\underset{OM}{|}}{\overset{\overset{O}{\|}}{P}}-O(CH_2CH_2O)_n$$

wherein
R is a hydrocarbon group having 8 to 22 carbon atoms;
n is 0 or an integer of from 1 to 10; and
M is hydrogen or an alkali metal, ammonium or amine salt forming group.

2. An aqueous shampoo as claimed in claim 1, in which the detergent is a $C_{10}$ to $C_{18}$ alkyl ether sulphate containing from 2 to 3 moles of ethylene oxide.

3. An aqueous shampoo consisting essentially of:
(a) from 5 to 30% by weight of a $C_{10}$ to $C_{18}$ alkyl ether sulphate containing from 2 to 3 moles of ethylene oxide;
(b) from 0.1% to 5% by weight of a polyglycol condensation resin which is a hardenable polycondensation product produced by reacting a polyamine compound having from 2 to 10 carbon atoms with an ether of polyoxyalkylene glycol having terminal halogens or hydroxyls and having from 2 to 4 carbon atoms in the alkylene units thereof, said polyamine reaction compounds having more than one hydrogen atoms attached to a nitrogen atom and being further reacted with a bifunctional aliphatic compound having functional groups selected from the group consisting of epoxide and α-halo-β-hydroxy-alkyl;

(c) from 0.1% to 3% by weight of a phosphate ester comprising a monoester of the formula

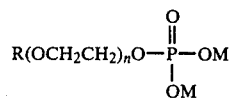

and/or a diester of the formula

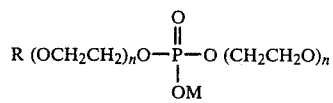

where
R is a hydrocarbon group having 8 to 22 carbon atoms;
n is 0 or an integer of from 1 to 10;
M is hydrogen or an alkali metal, ammonium or amine salt forming group; and
(d) water.

4. A method of treating hair, which comprises applying to the hair an effective amount of an aqueous shampoo according to claim 1.

5. A closed container or dispenser containing an aqueous shampoo according to claim 1.

* * * * *